United States Patent [19]

Crary

[11] Patent Number: 5,639,482
[45] Date of Patent: Jun. 17, 1997

[54] COMPOSITION FOR CONTROL AND PREVENTION OF DIABETIC RETINOPATHY

[76] Inventor: Ely J. Crary, Rte. 6, Box 634, Shallotte, N.C. 28459

[21] Appl. No.: 149,925

[22] Filed: Nov. 10, 1993

[51] Int. Cl.⁶ .................... A61K 33/04; A61K 31/525
[52] U.S. Cl. ................... 424/702; 514/251; 514/912
[58] Field of Search .................. 424/702; 514/251, 514/912

[56] References Cited

U.S. PATENT DOCUMENTS

| | | |
|---|---|---|
| 3,928,578 | 12/1975 | Burns et al. |
| 4,476,114 | 10/1984 | Pekkanen. |
| 4,668,515 | 5/1987 | Bankit et al. |
| 4,784,852 | 11/1988 | Johansson. |
| 4,988,517 | 1/1991 | El-Bayoumy et al. |
| 4,988,690 | 1/1991 | Revici. |
| 5,045,316 | 9/1991 | Kaplan. |

OTHER PUBLICATIONS

Medline Abstracts 93297181. (1993). Kahler et al.
Chemical Abstracts 101: 71450 (1984). Thornber et al.
Medical Hupotheses 13: 77–98, 1984 "Potential Clinical Applications for High–Dosage Nutritional Antioxidants" E. J. Crary, M. D.
"See Tomorrow Natural Sight" Dec. 22, 1992.
"Natural Sight" packet of tablets, Mar. 1993.

*Primary Examiner*—Zohreh Fay

[57] ABSTRACT

The present invention is a method of treating diabetic retinopathy and a means for preventing its reoccurence. This is accomplished by supplementing the diet of the diabetic with approximately 1000 mcg sodium selenite and 1000 IU vitamin E on a daily basis for between 24 and 35 days until the visual acuity of the diabetic improves. Thereafter a daily maintenance supplement of 250 mcg sodium selenite and 400 IU vitamin E can be used. In the initial supplement, 1000 mcg selenonthianone or 1000 mcg selenium yeast can be used although it is less effective and requires 2000 IU of vitamin E for positive results.

5 Claims, No Drawings

COMPOSITION FOR CONTROL AND PREVENTION OF DIABETIC RETINOPATHY

FIELD OF INVENTION

This invention relates to pharmaceutical composition and more particularly to the treating and prevention of diabetic retinopathy.

BACKGROUND OF INVENTION

It is known that the earliest pathological changes of diabetic retinopathy starts in the capillaries of the retina. The capillaries are made up of one cell thickness, such cells being muscle cells referred to as pericyte. The loss of function of these cells results in vascular leakage. The weakening of the pericyte shows up as microaneurysms and finally the breakage and death of the pericyte is seen as a hemorrhage.

Although there are some theories, it is not known how diabetes causes changes to the pericyte nor has it been known how to treat and prevent it.

Diabetic retinopathy takes several years to set up and is usually not seen before the patient has had the disease for at least 10 years. It is also known that once the pathology starts the process seems to speed up. The sequence of events from vascular leakage to hemorrhage and neovascularization may occur within one year in many patients. Apparently the pericyte has a reserve or ability to heal itself during the early years of the diabetic condition and only after repetitive assaults on the intracellular functions do they finally begin to break down. Also apparently each elevation of the patient's blood sugar causes intracellular functions to be changed or damaged in a small way.

If the pericyte can return to its normal function, this would result in a pericyte healing itself and preventing the pathology discussed above.

The rare earth metal selenium was at one time thought to be carcinogenic. Clinical tests and experiments in the last few years have refuted this earlier theory.

Selenite in various forms and in combination with other elements have been used for the treatment of various animal and human conditions such as the control of white muscle disease in mammals and the treatment of malignant tumors, arterial sclerosis and mental syndromes in the elderly, as a cancer inhibitor, to prevent various degenerative diseases in animals such as piglets, the treating of drug addiction, in compositions for inhibiting colon carcinogens and as a mineral supplement to maintain the health of mammals, particularly humans.

None of the prior art references, however, have been directed to treatment programs using a form of selenium in the treatment and prevention of macular edema of diabetic retinopathy.

The following references represent the closest prior art of which the inventor is aware:

CONCISE EXPLANATION OF REFERENCES

U.S. Pat. No. 3,928,578 to Burns et al discloses a composition for the control of white muscle disease by the administration of a combination of selenium compound and vitamin E. This muscle treatment was used in mammals, both beasts and humans and included examples of case histories of almost immediate results in relief from muscle related conditions.

U.S. Pat. No. 5,045,316 to Kaplan discloses a pharmaceutically active combination including an active combination of ionic selenium vanadium compound and thiosulphate or sulfite compound and optional selenium for the treating of malignant tumors, arteriosclerosis and mental syndromes in the elderly.

U.S. Pat. No. 4,784,852 to Johansson discloses a compound for human supply of selenium as a trace element admixed into a composition of vitamins E, $B_2$, $B_6$ and $B_{12}$ for relieving and healing inflammatory conditions as a result of surgical operations, micro organism induced inflammation, virus attacks and the like.

U.S. Pat. No. 4,476,114 to Pekkanen is an iron-selenium preparation used in the treatment of iron and selenium deficiencies, particularly in piglets.

U.S. Pat. No. 4,565,690 to Revici is a method for treating drug addiction including the administering of an anabolic agent containing bivalent negative selenium or sulfur.

U.S. Pat. No. 4,988,517 discloses a method and composition for inhibiting colon cardinogenesis and includes the use of a selenium dependent glutathione peroxidase.

U.S. Pat. No. 4,668,515 to Bankit et al discloses a method and composition for sodium selenite administration in the form of a flavored drink containing ascorbic acid and citric acid.

Medical Hypotheses 13: 77–98, 1984 entitled "Potential Clinical Applications for High-Dosage Nutritional Antioxidants" discusses the possible advantages of vitamin C, E, and selenium as dietary supplements.

"See Tomorrow Natural Sight" is pamplet prepared by the present inventor.

"Natural Sight" packet of tablets is a sample packet sold to patients by the inventor.

BRIEF DESCRIPTION OF INVENTION

Although selenium and vitamin E have been used for the treatment of various diseases and conditions in mammals, both beasts and humans, and these compounds have been used in combination with other compounds in the treatment of diabetic retinopathy and recurrent macular edema, the use of these two compounds alone in predetermined dosages has not been suggested.

After much research and study into the treatment and prevention of diabetic retinopathy, the present invention has been developed which uses predetermined amounts of sodium selenite, selenonethianone or selenium yeast in combination with vitamin E to control and prevent early pathologic changes in the retina and can be used for the treatment of more advanced degeneration.

In view of the above, it is an object of the present invention to provide a method of preventing of diabetic retinopathy by supplementing the diet with predetermined amounts of selenium and vitamin E.

Another object of the present invention is to treat advanced diabetic retinopathy with a diet of predetermined amounts of specific types of selenium and vitamin E.

Another object of the present invention is to provide a diet supplement for diabetics by giving them a predetermined amount of selenium selected from the group consisting of sodium selenite, selenonethianone and selenium yeast in combination with vitamin E.

Other objects and advantages of the present invention will become apparent and obvious from a study of the following description and the accompanying drawings which are merely illustrative of such invention.

DETAILED DESCRIPTION OF INVENTION

As a result of extensive research, it has been discovered that 1,000 micrograms (mcg) of sodium selenite and 2,000 International units (IU) of vitamin E will cause the complications of capilliary leakage and bleeding in the diabetic to stop in 24 to 36 days. If the diet continues, further leakage and bleeding will be prevented.

Leakage can also be stopped in approximately 60 days with 250 mcg of sodium selenite and 400 IU of vitamin E. The same results have been achieved in 130 to 180 days using 1,000 mcg of seleononthianone or 1,000 mcg of selenium yeast and 2,000 IU of vitamin E.

The following case histories of the effectiveness of the present preparation in treating diabetic patients are as follows:

1. 19 year old white male with a history of diabetes mellitus since eight years of age and on 65 IU of insulin daily. On the first eye examination the visual acuity was OD 20/60, OS 20/40 with microaneurysms present and an occasional small blot hemorrhage, background retinopathy and mild diffused macula edema. The patient was started on a daily diet of 1,000 mcg sodium selenite and 1,000 IU of vitamin E. On the 25th day the patient called in and stated that his sight had improved. An examination revealed visual acuity OD 20/20, OS 20/20 and the macula edema had cleared. The selenium and vitamin E was discontinued on the 30th day. 84 days after stopping the selenium and vitamin E the patient noted blurred sight. Examination on the 85th day showed return of diffuse macula edema and visual acuity of OD 20/60, OS 20/40. The patient was restarted on 1,000 mcg selenium and 1,000 IU of vitamin E. 25 days after restart, the sight returned. An examination revealed the edema cleared and visual acuity of 20/20 in each eye. The patient stayed on selenium and vitamin E for three years with stable 20/20 sight and no progression of retinopathy. The patient thereafter left the area and discontinued the treatment. He returned 19 months later with advanced diabetic retinopathy with retinal and vitreous hemorrhaging and neovascularization. He was lasered but his eyes continued to generate with diabetic retinopathy.

2. 35 year old female with history of adult type II diabetes controlled with Oranase, diet and exercise. When examined she had diffuse macula edema, visual acuity OD 20/60, OS 20/80 and she could no longer see well enough to continue her work as a secretary. Started on 1,000 mcg selenium and 1,000 IU vitamin E. 24 days after starting she called and said that her sight had cleared. Examination that day determined that she had visual acuity of 20/20 OU. Also, the macula edema of both retinas had cleared. The selenium and vitamin E were stopped on the 30th day. The patient called on the 84th day after stopping treatment and stated that sight was down again. Examination the same day showed visual acuity of OD 20/60, OS 20/80 and the macula edema had returned. The patient restarted on the supplement and on the 24th day her sight returned. The process was repeated six times with the same results. The patient is now maintaining a daily supplement of 250 mcg sodium selenite and 400 IU vitamin E. Her eyesight is 20/20 and she has multiple small scar areas in the periphery of her retina. She has continued to be monitored over an extended period with no change.

3. 80 year old white male adult with type II diabetic visual acuity of OD 20/200, OS 20/100 and diffuse macula edema. 1,000 mcg sodium selenite and 1,000 IU vitamin E were started. On the 32nd day the patient called and stated he had noticed improvement of his sight. Examination the next day showed visual acuity of OD 20/100, OS 20/40 and the macula edema had cleared. The remaining decrease visual acuity was due to age related macula degeneration.

4. 54 year old white male type II taking Diabinase, diet and exercise. On examination his visual acuity was OD 20/80, OS 20/80 and showed diffuse macula edema and background diabetic retinopathy of microaneurysms and rare blot hemorrhage. No retinal or vitreous hemorrhages and no neovasularization. He was started on 1,000 mcg sodium selenite and 1,000 IU of vitamen E. On the 28th the patient called in and stated that he could see better. On examination the next day, visual acuity was OD 20/30, OS 20/25. The supplementation was discontinued. 89 days later the patient called and complained that sight was failing again. On examination, the acuity was OD 20/80, OS 20/80 with macula edema present. The supplement was restarted and visual acuity returned on the 29th day. The patient's sight remained the same for four years until he moved from the area and contact with him was lost.

In other case histories, it has been determined that in addition to 1,000 mcg sodium selenite and 1,000 IU vitamin E giving positive results between 24 and 35 days, the same results can be achieved in approximately 60 days with 250 mcg sodium selenite and 400 IU vitamin E. With 1,000 mcg selenonthianone or 1,000 mcg silenium yeast and 2,000 IU vitamin E, positive results have been noted between 120 and 180 days.

To get the results indicated above, the supplement must be taken on a daily basis.

From the above it can be seen that the present invention provides a simple and yet effective dietary supplement that can control and prevent diabetic retinopathy from developing and can be used for the treatment of more advanced degeneration.

The present invention may, of course, be carried out in other specific ways other than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. A method of treating and preventing macular edema of human diabetic retinopathy comprising: supplementing the diet of diabetics with between 250 and 1000 mcg selenium; and between 400 and 2,000 IU vitamin E on a daily basis.

2. A method of treating humans susceptible to macular edema of diabetic retinopathy comprising: adding a diet supplement, on a daily basis, 1,000 mcg sodium selenite and 2000 IU vitamin E whereby the complications of capillary leakage and bleeding in a diabetic can be stopped in 24 to 36 days.

3. A method of treating humans susceptible to macular edema of diabetic retinopathy comprising: adding a diet supplement, on a daily basis, 250 mcg sodium selenite and 400 IU vitamin E whereby the complications of capillary leakage and bleeding in a diabetic can be stopped in approximately 60 days.

4. A method of treating humans susceptible to macular edema of diabetic retinopathy comprising: adding a diet supplement, on a daily basis, 2000 IU vitamin E and 1000 mcg selenium selected from the group consisting of selenothianone and selenium yeast whereby the complications of capillary leakage and bleeding in a diabetic can be stopped in approximately 120 to 180 days.

5. A method preventing the reoccurrence of macular edema of diabetic retinopathy in humans comprising: providing a daily supplemental diet of 250 mcg sodium selenite and 400 IU vitamin E.

* * * * *